(12) United States Patent
Coe et al.

(10) Patent No.: US 11,154,429 B2
(45) Date of Patent: *Oct. 26, 2021

(54) METHOD FOR FABRICATING ABSORBENT ARTICLES

(71) Applicant: The Procter & Gamble Company, Cincinnati, OH (US)

(72) Inventors: Richard George Coe, Cincinnati, OH (US); Kevin Gerard Muhs, Hamilton, OH (US); Robert Karl Isburgh, Loveland, OH (US); Pietro Cecchetto, Fairfield, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/690,468

(22) Filed: Nov. 21, 2019

(65) Prior Publication Data

US 2020/0085634 A1    Mar. 19, 2020

Related U.S. Application Data

(63) Continuation of application No. 16/014,608, filed on Jun. 21, 2018, now Pat. No. 10,531,989, which is a
(Continued)

(51) Int. Cl.
*A61F 13/00* (2006.01)
*B29C 65/00* (2006.01)
(Continued)

(52) U.S. Cl.
CPC .. *A61F 13/15699* (2013.01); *A61F 13/15707* (2013.01); *A61F 13/15723* (2013.01);
(Continued)

(58) Field of Classification Search
CPC .......... A61F 13/00; A61F 13/10; A61F 13/15; A61F 13/156; A61F 13/1569;
(Continued)

(56) References Cited

U.S. PATENT DOCUMENTS 7,402,723 B2    7/2008  Stone
7,967,801 B2    6/2011  Hammons
(Continued)

OTHER PUBLICATIONS

PCT Search Report and Written Opinion for PCT/US2014/071017 dated Feb. 9, 2015.
(Continued)

*Primary Examiner* — Jacob T Minskey
*Assistant Examiner* — Matthew Hoover
(74) *Attorney, Agent, or Firm* — George H. Leal; Amanda T Barry

(57) ABSTRACT

The present invention relates to a method for fabricating absorbent article having multiple layers, and deformed zones of targeted performance, and colored regions, the method comprising the steps of forming discrete features on at least one layer, printing colored regions on at least one layer, integrating multiple layers to form an absorbent assembly, and cutting the absorbent assembly into individual absorbent articles, wherein the steps are carried out continuously.

20 Claims, 6 Drawing Sheets

Related U.S. Application Data continuation of application No. 15/375,710, filed on Dec. 12, 2016, now Pat. No. 10,022,275, which is a continuation of application No. 14/574,444, filed on Dec. 18, 2014, now Pat. No. 9,549,857, which is a continuation-in-part of application No. 14/512,946, filed on Oct. 13, 2014, now abandoned.

(60) Provisional application No. 61/918,670, filed on Dec. 20, 2013.

(51) Int. Cl.
| | | |
|---|---|---|
| *A61F 13/15* | (2006.01) | |
| *B29C 65/08* | (2006.01) | |
| *B29C 65/18* | (2006.01) | |
| *B29C 65/48* | (2006.01) | |
| *B29C 65/56* | (2006.01) | |
| *B29K 105/00* | (2006.01) | |
| *B29L 31/48* | (2006.01) | |

(52) U.S. Cl.
CPC .. *A61F 13/15731* (2013.01); *A61F 13/15739* (2013.01); *B29C 65/08* (2013.01); *B29C 65/18* (2013.01); *B29C 65/48* (2013.01); *B29C 65/56* (2013.01); *A61F 2013/1591* (2013.01); *A61F 2013/15869* (2013.01); *A61F 2013/15878* (2013.01); *B29K 2105/256* (2013.01); *B29K 2995/0068* (2013.01); *B29K 2995/0069* (2013.01); *B29K 2995/0092* (2013.01); *B29L 2031/4878* (2013.01); *Y10T 156/1044* (2015.01)

(58) Field of Classification Search
CPC .............. A61F 13/15699; A61F 13/157; A61F 13/157; A61F 13/15707; A61F 13/1572; A61F 13/15723; A61F 13/1573; A61F 13/15731; A61F 13/15739; B29C 65/00; B29C 65/08; B29C 65/10; B29C 65/18; B29C 65/40; B29C 65/48; B29C 65/50; B29C 65/56

See application file for complete search history.

(56) References Cited

U.S. PATENT DOCUMENTS

| | | |
|---|---|---|
| 8,691,041 B2 | 4/2014 | Oetjen |
| 8,708,687 B2 | 4/2014 | Coe et al. |
| 9,549,857 B2 | 1/2017 | Coe et al. |
| 10,022,275 B2 | 7/2018 | Coe |
| 10,531,989 B2 | 1/2020 | Coe et al. |
| 2004/0122395 A1* | 6/2004 | Stone ................ A61F 13/512 604/383 |
| 2010/0036346 A1* | 2/2010 | Hammons ......... A61F 13/51305 604/378 |
| 2011/0094669 A1* | 4/2011 | Oetjen ............. A61F 13/15731 156/250 |
| 2011/0264065 A1 | 10/2011 | Arora et al. |
| 2015/0173963 A1 | 6/2015 | Coe et al. |
| 2015/0173964 A1 | 6/2015 | Coe et al. |

OTHER PUBLICATIONS

All Office Actions for U.S. Appl. No. 14/512,946, filed Oct. 13, 2014.
All Office Actions for U.S. Appl. No. 14/574,444, filed Dec. 18, 2014.
All Office Actions for U.S. Appl. No. 15/375,710, filed Dec. 12, 2016.
All Office Actions for U.S. Appl. No. 16/014,608, filed Jun. 21, 2018.

* cited by examiner

METHOD FOR FABRICATING ABSORBENT ARTICLES

FIELD OF THE INVENTION

The present invention relates to methods for fabricating absorbent articles. Specifically, the method can be used to fabricate absorbent articles having a colored region and a deformed topsheet in a continuous process.

BACKGROUND OF THE INVENTION

Absorbent articles such as sanitary napkins and female adult incontinence articles that function to collect fluid discharged from a woman's vagina or urethra often include a deformed surface region and a colored region in the absorbent article.

A colored region on or below a top surface of an absorbent article that is visible through a topsheet can provide functional and perceptional advantages. The colored region can overcome a problem of unsightly stain during, for example, a woman's menstrual period. The colored region on a layer below the topsheet which can be viewed through the topsheet can also provide for a perception of depth and greater fluid storage capacity within the absorbent article. In addition, by including a colored region in the central portion of the absorbent article, manufacturers of absorbent articles may effectively teach consumers that the central portion of the absorbent article is where the fluid collected should reside.

Meanwhile, various fluid handling demands on different portions of an absorbent article, different physical interactions between portions of an absorbent article and portions of a wearer's body, and different moisture and chemical environments of different portions of a wearer's crotch region create unique needs for different regions of the topsheet. Some absorbent articles designed to have a topsheet with deformed regions that are arranged to provide fluid handling benefits where needed and/or skin comfort benefits where needed are, for example, disclosed in WO 10/17360; WO 10/17362; and WO 10/17351.

Provision of a colored region and/or deformed regions on a web has been carried out separately from an absorbent article fabrication.

In many cases to provide best functionality of absorbent articles, it is best to provide each step of the manufacturing process next to each other and in the right sequence so that one does not have issues with performance of the absorbent articles that could occur if made separately. For instance, formation of features in a topsheet far apart or in a different sequence may cause weakening of the topsheet structure, thereby causing tearing in use or during the manufacturing process. Further, separation of unit steps of feature formations may increase the possibility that some or many features closely co-located in a topsheet formed in different unit steps overlap which leads to increased aperture size which would cause rewet problems.

Accordingly, there is a need for a process which can provide zones of targeted performance, and colored regions in a high-speed continuous operation.

SUMMARY OF THE INVENTION

The present invention is directed to a method for fabricating absorbent articles having multiple layers, and deformed zones of targeted performance, and colored regions.

DETAILED DESCRIPTION OF THE INVENTION

Figure 1:
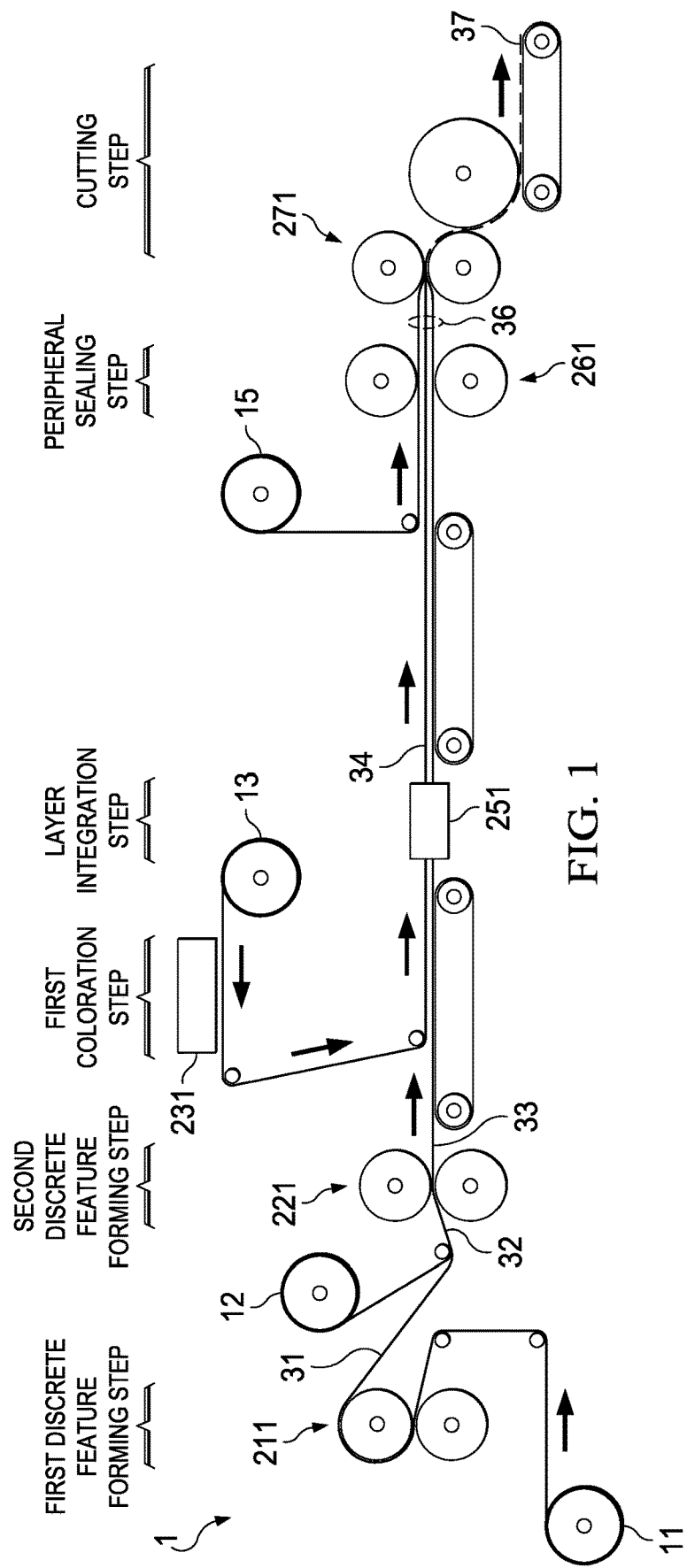
FIG. 1 is a schematic representation of a process of the present invention.

The term "absorbent article", as used herein, includes disposable articles such as sanitary napkins, panty liners, diapers, adult incontinence articles, and the like. Such absorbent articles are intended for the absorption of body liquids, such as menses or blood, vaginal discharges, urine, and feces. Various absorbent articles described above will typically comprise a liquid permeable topsheet, a liquid impermeable backsheet joined to the topsheet, and an absorbent core between the topsheet and backsheet.

The term "aperture", as used herein, refers to a hole. The apertures can either be punched cleanly through the web so that the material surrounding the aperture lies in the same plane as the web prior to the formation of the aperture, or holes formed in which at least some of the material surrounding the opening is pushed out of the plane of the web. In the latter case, the apertures may resemble a protrusion or depression with an aperture therein.

The term 'color' as referred to herein includes any color, i.e., white, black, red, blue, violet, orange, yellow, green, and indigo as well as different shades thereof or mixtures thereof.

The term "component" of an absorbent article, as used herein, refers to an individual constituent of an absorbent article such as a topsheet, acquisition layer, liquid handling layer, absorbent core or layers of absorbent cores, backsheets, and barriers such as barrier layers and barrier cuffs, and functional or aesthetic design elements such as colored regions, channels, and features formed on a topsheet.

The term "comprising", as used herein and in the claims, is inclusive or open-ended and does not exclude additional unrecited elements, compositional components, or method steps.

The term "discrete", as used herein, means distinct or unconnected. When the term "discrete" is used relative to forming elements on a forming member, it is meant that the distal (or radially outwardmost) ends of the forming elements are distinct or unconnected in all directions, including in the machine and cross-machine directions (even though bases of the forming elements may be formed into the same surface of a roller, for example).

The term "forming elements", as used herein, refers to any elements on the surface of a forming member such as a roller that are capable of deforming a web. The term "forming elements" includes both continuous or non-discrete forming elements such as the ridges and grooves on ring rollers, and discrete forming elements.

The term "joined", as used herein, refers to the condition where a first component is affixed, or connected, to a second component either directly; or indirectly, where the first component is affixed, or connected, to an intermediate component which in turn is affixed, or connected, to the second component. The joined condition between the first component and the second component is intended to remain for the life of the absorbent article.

The term "machine direction" or "MD", as used herein, refers to the path that material, such as a web, follows through a manufacturing process, while the term "cross machine direction" or "CD" is the direction substantially perpendicular to the MD and in the plane generally defined by the web. Directions within 45 degrees of the cross direction are considered to be cross directional.

The term "nonwoven", as used herein, refers to a material having a structure of individual fibers or threads which are interlaid, but not in a repeating pattern as in a woven or knitted fabric, which do not typically have randomly oriented fibers. Nonwoven has been formed from many processes, such as, for example, meltblowing processes, spunbonding processes, hydroentangling, and bonded carded web processes, including carded thermal bonding. The constituent fibers of a nonwoven can be polymer fibers, and can be monocomponent, bicomponent, and/or biconstituent, and a mixture of different fiber types.

The term "odor control composition", as used herein, refers to such compositions usually contain, sometimes along with conventional perfume ingredients, ingredients which are able to chemically react with the malodorant molecules released from the body fluids (such as ammonia) thus neutralizing the source of the malodor, and/or ingredients which are able to interact with nose receptors so that their perception of the malodorant molecules is reduced.

The term "phase", as used herein, refers to the positional relationship between two or more parts of a machine that performs repetitive motion. For example, phase may refer to the relative position of a punch that stamps apertures into a component used in the manufacturing process. When utilized as verbs, the terms "phasing," "phased," "phase," and the like refer to the act of changing the phase of a device from one phase to another. For example, the act of phasing a roller may refer to advancing or retarding the rotation of the roller about its primary axis.

The term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

The term "tuft", as used herein, refers to a particular type of protrusion. Tufts may have a tunnel-like configuration, and in some cases may be open at one or both of their ends.

The term "upper", as used herein, refers to absorbent members, such as layers, that are nearer to the wearer of the absorbent article during use, i.e. towards the topsheet of an absorbent article; conversely, the term "lower" refers to absorbent members that are further away from the wearer of the absorbent article towards the backsheet.

The term "web", as used herein, refers to any suitable deformable material, such as a woven, nonwoven, film, combination, or laminate of any of the foregoing materials.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

Absorbent Article

Absorbent articles manufactured by a method according to the present invention comprise a liquid permeable deformed topsheet; a liquid permeable colored sheet, and a liquid impermeable backsheet joined to the topsheet, wherein the topsheet comprises a first layer and a second layer, and have a plurality of first discrete features and a plurality of second discrete features; wherein the colored sheet has a first colored region and comprises a colored sheet web; and wherein the backsheet comprises a backsheet web.

Each of the first layer and the second layer can be a polymer film, a nonwoven, a composite comprising a polymer film or a nonwoven, or laminate comprising a polymer film or a nonwoven. In one embodiment, the first layer is a first polymer film and the second layer is selected from a nonwoven and a second polymer film. In the embodiment the first polymer and second polymer films may be the same or different polymer films. In another embodiment, the first layer is a first nonwoven and the second layer is selected from a polymer film and a second nonwoven. In this embodiment, the first and the second nonwovens may be the same or different materials.

In one embodiment, when at least one of the first and second layers is a polymer film, the polymer film is a polymer film including materials normally extruded or cast as films such as polyolefins, nylons, polyesters, and the like. Such films can be thermoplastic materials such as low density polyethylene, medium density polyethylene, high density polyethylene, linear low density polyethylene, polypropylenes and copolymers and blends containing substantial fractions of these materials.

In another embodiment, when at least one of the first and second layers is a nonwoven, the nonwoven constituting the topsheet is a colored nonwoven.

The polymer film can have a plurality of discrete extended elements. Patent publications disclosing such a plurality of discrete extended elements include WO 01/76842; WO 10/104996; WO 10/105122; WO 10/105124 and US20120277701A1. In one embodiment, the polymer film can have a plurality of discrete extended elements comprising open proximal ends, open or closed distal ends, and sidewalls, wherein the discrete extended elements comprise thinned portions at the distal ends of the discrete extended elements and/or along the sidewalls of the discrete extended elements, and wherein the discrete extended elements have a diameter of less than about 500 microns; the discrete extended elements have an aspect ratio of at least about 0.2;

and/or the polymer film comprises at least about 95 discrete extended elements per square centimeter.

In the present invention, the colored sheet comprising a colored sheet web may function as a secondary topsheet in an absorbent article. The colored sheet web can be any sheet material that allows a colored region to be readily seen from a body-facing surface of an absorbent article, and can be manufactured from a wide range of materials such as woven, nonwoven materials, latex or thermally bonded airlaid materials, polymeric materials such as apertured formed thermoplastic films, apertured plastic film, hydro-formed thermoplastic films, porous foams, reticulated foams, reticulated thermoplastic films and thermoplastic scrims.

In the present invention, a backsheet web can be any backsheet material commonly used for absorbent articles such as polyolefinic films like polyethylene, polypropylene and a combination thereof. In some embodiments, the backsheet may be impervious to malodorous gases generated by absorbed bodily discharges, so that the malodors do not escape. The backsheet may or may not be breathable.

An absorbent article manufactured by the method according to the present invention has a background region and a first colored region, and optionally a second colored region being viewable from the body-facing surface of the absorbent article. The background region is visually distinguishable from the first colored region and the optional second colored region. The background region can be white or any other color visually distinguishable from the first colored region and second colored region. The first colored region and the optional second colored region can be visually distinguishable in terms of color and/or shade of a color. Colors are believed to be visually distinguishable if there is a ΔE calculated according to the equation below between the two colors of at least about 1. The first colored region and the second colored region, respectively, can have e a multiple colored regions. The multiple colored regions can be visually distinguishable in terms of color and/or shade of a color.

The color of the first colored region, the second colored region and background region are measured by the reflectance spectrophotometer according to the method disclosed in WO 11/25486. The difference in color is calculated using the L*, a*, and b* values by the formula $\Delta E=[(L^*_X-L^*_Y)^2+(a^*_X-a^*_Y)^2+(b^*_X-b^*_Y)^2]^{1/2}$. Herein, the 'X' in the equation may represent the first colored region, the second colored region or the background region, and 'Y' may represent the color of another region against which the color of such region is compared. X and Y should not be the same two points of measurement at the same time.

The absorbent articles of the present invention may further comprise an absorbent core joined with the topsheet, the backsheet, or both in any manner as is known by attachment means such as those well known in the art. Embodiments of the present invention are envisioned wherein portions of the entire absorbent core are unattached to either the topsheet, the secondary topsheet, the backsheet, or more than one of these layers. The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015.

The absorbent core can comprise superabsorbent materials such as absorbent gelling materials (AGM), including AGM fibers, as is known in the art.

The absorbent articles of the present invention may have a pair of flaps on longitudinal sides of a body-facing surface for folding around and securing the absorbent article to the undergarment. Flaps, if used, can be integral extensions of at least one layer of the topsheet or the backsheet or both, and they can be symmetric about a longitudinal axis, transverse axis, or both of the absorbent articles. For example, the flaps may comprise the first layer of the topsheet and a backsheet. Alternatively, the flaps may comprise the topsheet comprising a first layer and a second layer, and the backsheet. The layers in the flaps can be laminated by either adhesive or thermally bonded means, where thermal bonding includes but is not restricted to technologies such as ultrasonic bonding, cold pressure bonding, and hot pressure bonding. The flaps may have a plurality of third discrete features thereon. The third discrete features may be the same features as one of the first and the second discrete features, or different features from the first and the second discrete features. The plurality of third discrete features may be formed simultaneously with at least one of the plurality of first discrete features and the plurality of second discrete features. For example, a plurality of third discrete features may be depressions formed toward a garment facing side of a topsheet. In one embodiment, depression type of third discrete features can be formed on a first layer film simultaneously with a plurality of first discrete features when the plurality of first discrete features are apertures toward a garment facing side of a topsheet.

The invention is applicable to the production of absorbent articles from discrete components, and it is particularly advantageous for the production of absorbent articles from at least one continuous sheet or web.

A schematic representing a method according to the invention is depicted in FIG. 1. In FIG. 1, the machine direction is from left to right. The method of the invention may form the absorbent article upside down. Alternatively, the absorbent article can be formed top-side up.

Figure 3:
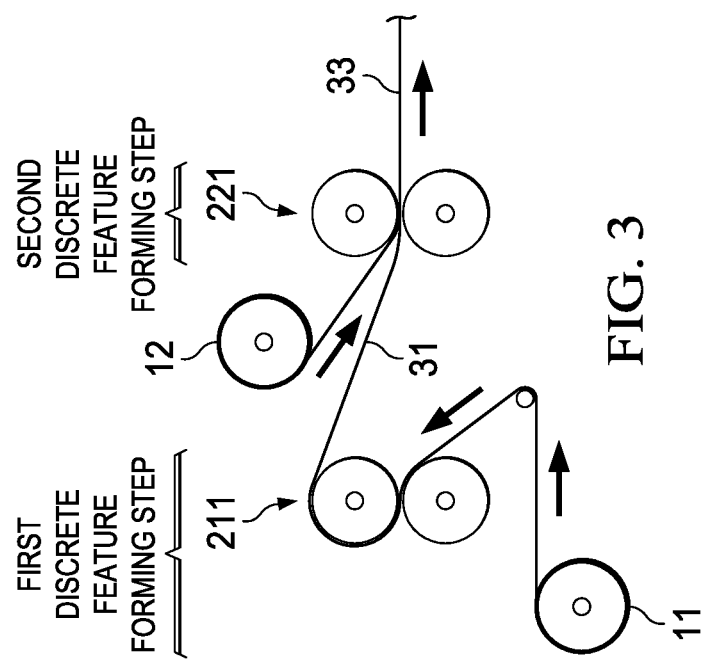
FIG. 3 is schematic representation of another means of forming a second discrete feature as a separate forming step of a process of the present invention.

The process 1 carried out according to the example in FIG. 1 comprises supplying a first layer 11 to a first discrete feature forming unit 211 to form a deformed first layer 31. Though the process shown in FIG. 1 indicates a step of formation of a composite of the first and second layers and a step of second discrete features formation are carried out sequentially, these two steps can be carried out simultaneously as shown in FIG. 3.

In one example, the first discrete feature forming units 211 may comprise a pair of two generally cylindrical rollers wherein at least one of the two rollers has discrete feature forming elements on its surface.

Figure 4:
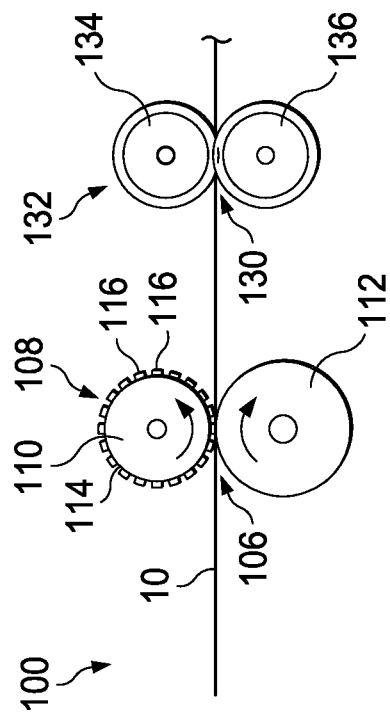
FIG. 4 is a schematic representation of an exemplary process for selectively aperturing a web in the process of the present invention.
Figure 7:
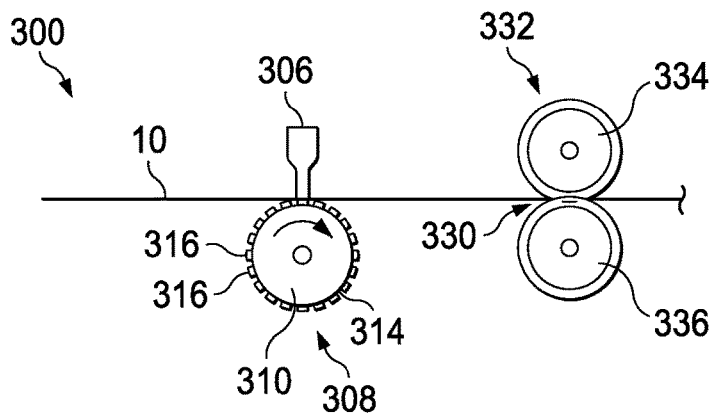
FIG. 7 is a schematic representation of another process for selectively aperturing a web in the process of the present invention.

In another example when the first discrete features are apertures, the first discrete feature forming units 211 may comprise a means for weakening a web, first layer 11 in this case, at a plurality of locations to create a plurality of weakened, melt-stabilized locations, and a means for applying a tensioning force to the web to rupture the web at the plurality of weakened, melt-stabilized locations creating a plurality of apertures in the web coincident with the plurality of weakened, melt-stabilized locations. Referring to FIGS. 4 and 7, a means for weakening a web 10 at a plurality of locations to create a plurality of weakened may be a web weakening roller arrangement 108 or 308, and a means for applying a tensioning force to the web 10 to rupture the web 10 at the plurality of weakened may be an incremental stretching system 132 or 332 shown in FIGS. 4 and 7.

Then, supplying a second layer 12 onto the deformed first layer 31 to form a composite 32 of the deformed first layer 31 and the second layer 12, feeding the composite 32 to a second discrete feature forming unit 221 to form a deformed composite 33. In one example, the second discrete feature forming units 221 may comprise a pair of two generally cylindrical rollers wherein at least one of the two rollers has discrete feature forming elements on its surface.

Separately, a colored sheet web 13 is provided with a first colored region in a first coloration unit 231, and then is supplied onto a second layer side of the deformed composite 33. When the colored sheet web 13 has a colored region before conducting the first coloration step, the first coloration step may be skipped, or still employed to provide an additional colored region on the colored sheet web 13. Then, the colored sheet web 13 and the deformed composite 33 are integrated to form an integrated composite 34 in an integration unit 251. And then, a backsheet web 15 is supplied onto a colored sheet web side of the integrated composite 34 and integrated by peripheral sealing along a peripheral line of an absorbent article in a peripheral seal unit 261 to form an absorbent article assembly 36. The absorbent article assembly 36 is cut in a cutting unit 271 into individual absorbent articles 37.

Figure 2:
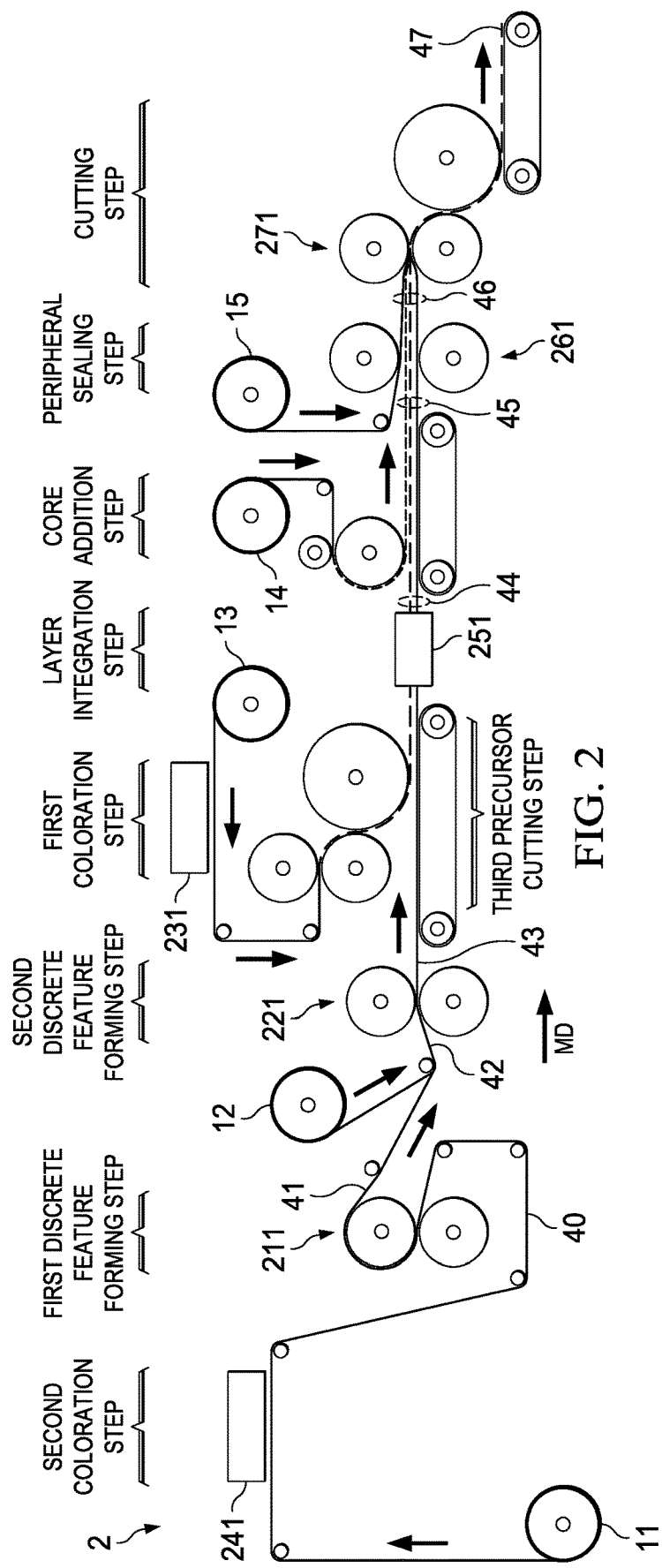
FIG. 2 is a schematic representation of another embodiment of a process of the present invention.

Referring to FIG. 2, there is shown another example of a method according to the invention with several optional steps. In the process 2 carried out in FIG. 2, initially a first layer 11 is produced with a second colored region in a second coloration unit 241. The second colored region can be provided on either side of the first layer 11. Alternatively, the second colored region can be provided in a second layer 12. When the first layer 11 or the second layer 12 already has a second colored region before conducting the second coloration step, the second coloration step may be skipped, or still employed to provide additional colored region on the first layer 11 or the second layer 12.

A colored polymer film 40 is fed into a first discrete feature forming unit 211 to form a deformed first layer 41. Then, the second layer 12 is supplied onto the deformed first layer 41 to form a composite 42 of the deformed first layer 41 and the second layer 12, and the composite 42 is fed into a second discrete feature forming unit 221 to form a deformed composite 43. In one example, the first and second discrete feature forming units 211 and 221, respectively, may comprise a pair of two generally cylindrical rollers wherein at least one of the two rollers in each unit has discrete feature forming elements on its surface.

In another example, when the first discrete features are apertures, the first discrete feature forming units 211 may comprise a means for weakening a web, colored first layer 40 in this case, at a plurality of locations to create a plurality of weakened, melt-stabilized locations, and a means for applying a tensioning force to the web to rupture the web at the plurality of weakened, melt-stabilized locations creating a plurality of apertures in the web coincident with the plurality of weakened, melt-stabilized locations. Referring to FIGS. 4 and 7, a means for weakening a web 10 at a plurality of locations to create a plurality of weakened may be a web weakening roller arrangement 108 or 308, and a means for applying a tensioning force to the web 10 to rupture the web 10 at the plurality of weakened may be an incremental stretching system 132 or 332 shown in FIGS. 4 and 7.

A step of forming the composite 42 and a step of forming the second discrete features can be carried out sequentially as illustrated in FIG. 2 or simultaneously as shown in FIG. 3. Then, the colored sheet web 13 is supplied onto the second layer side of the deformed composite 43. The colored sheet web 13, before being supplied onto the deformed composite 43 to form an integrated composite 44, is provided with a first colored region in a first coloration unit 231, and may be cut into a predetermined size and shape, then is supplied onto a second layer side of the deformed composite 43. When the colored sheet web 13 already has a first colored region before conducting the first coloration step, the first coloration step may be skipped, or still employed to provide additional colored region on the colored sheet web 13. Then, the deformed composite 43 and the colored sheet web 13 are integrated to form an integrated composite 44, and an absorbent core 14, which can be a continuous sheet or in a determined size and shape, is supplied onto a colored sheet web side of the integrated composite 44 to form a core layered composite 45. A backsheet web 15 is supplied and adhered onto an absorbent core side of the core layered composite 45, and integrated by peripheral sealing along a peripheral line of an absorbent article in a peripheral seal unit 261 to form an absorbent article assembly 46. The absorbent article assembly 46 is then cut by a cutting unit 271 into individual absorbent articles 47.

Figure 9:
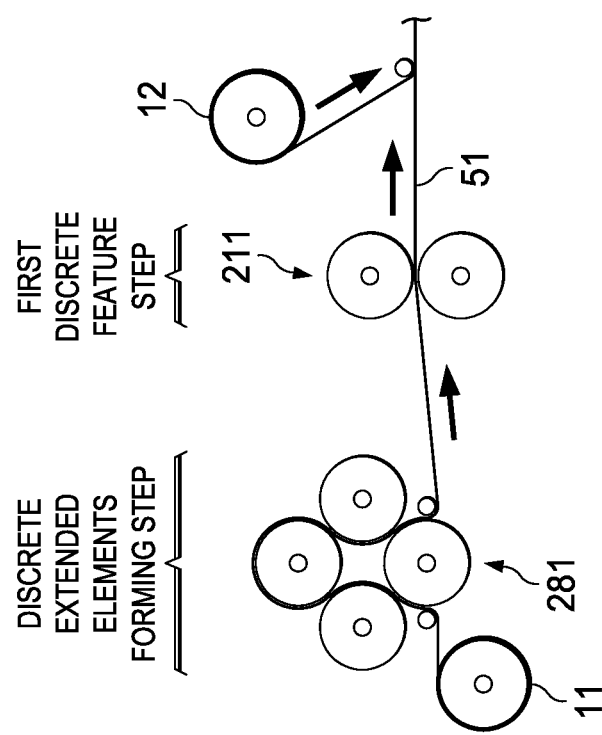
FIG. 9 is a schematic representation of discrete extended elements forming step of a process of the present invention.

The first layer 11 can have a plurality of discrete extended elements which may be formed in a step continuously proceeding with a method according to the invention. Formation of a plurality of discrete extended elements can be carried out prior to formation of a plurality of first discrete features. Referring to FIG. 9, the first layer 11 is fed into a discrete extended elements forming unit 281 to form a plurality of discrete extended elements before forming a deformed first layer 51. Examples of the discrete extended elements forming unit 281 and discrete extended elements forming processes are disclosed in WO 10/105009; WO 10/105002; WO 10/105017; WO 11/112213; and WO 12/148936.

Formation of First and Second Discrete Features

In the present invention, the first discrete features and the second discrete features may be of any suitable configuration. Suitable configurations for the features include, but are not limited to: apertures; ridges (continuous protrusions) and grooves (continuous depressions); tufts; columnar shapes; dome-shapes, tent-shapes, volcano-shapes; features having plan view configurations including circular, oval, hour-glass shaped, star shaped, polygonal, polygonal with rounded corners, and the like, and combinations thereof. Polygonal shapes include, but are not limited to rectangular (inclusive of square), triangular, hexagonal, or trapezoidal. In one embodiment, the first discrete features are features selected from the group consisting of apertures, protrusions, depressions, tufts, and combinations thereof, and the second discrete feature are features selected from the group consisting of apertures, protrusions, depressions, tufts, and combinations thereof. In another embodiment, the first discrete features are apertures and the second features are tufts.

The first discrete features and the second discrete features may differ from each other in terms of one or more of the following properties: type, shape, size, aspect ratio, edge-to-edge spacing, height or depth, density, color, surface treatment (e.g., lotion, etc.), number of web layers within the features, and orientation (protruding from different sides of the web). The term "type", as used herein, refers to whether the feature is an aperture, a protrusion such as a tuft and other kind of protrusion, or a depression.

In the present invention, discrete features may be of any suitable size. Typically, either the first features or the second features will be macroscopic. In some embodiments, the first features and the second features will both be macroscopic.

The plan view area of the individual features may, in some embodiments of the web, be greater than or equal to about 0.5 mm², 1 mm², 5 mm², 10 mm², or 15 mm², or lie in any range between two of these numbers. The methods described herein can, however, be used to create first features and/or second features that are microscopic which have plan view areas less than 0.5 mm².

Various methods and apparatuses for deforming webs by forming discrete features on webs known in the art can be utilized to form the first and the second discrete features in the present application. Patents disclosing such methods include: U.S. Pat. Nos. 4,189,344; 4,276,336; 4,609,518; 5,143,679; 5,562,645; 5,743,999; 5,779,965; 5,998,696; 6,332,955; 6,739,024; US Patent Application Publication 2004/0110442 A1; EP 1 440 197 B1; U.S. Pat. No. 6,916,969; US Patent Application Publication No. 2006/0151914 A1; U.S. Pat. Nos. 7,147,453; 7,423,003; 7,323,072; US Patent Application Publication No. 2006/0063454 A1; US Patent Application Publication No. 2007/0029694 A1; US Patent Application Publication No. 2008/0224351 A1; US Patent Application Publication No. 2009/0026651 A1; U.S. Pat. No. 7,521,588; US Patent Application Publication No. 2010/0201024 A1; WO2012/148980; WO2012/149074; WO2012/148935; and WO2012/148946.

One type of features preferred for at least one of the first and the second discrete features in the present invention are apertures. Apertures in a topsheet in an absorbent article may enhance penetration of body exudates through the topsheet into the underlying secondary topsheet or absorbent core. Various methods and apparatuses for forming apertures are disclosed in the patent literature. Patents disclosing such methods include: U.S. Pat. Nos. 8,241,543, 3,355,974; 2,748,863 and 4,272,473 disclosing aperture forming methods using apparatus having heated aperture forming elements; U.S. Pat. No. 5,628,097 disclosing a method for selectively aperturing a nonwoven web or laminate of a nonwoven web and a polymeric film by weakening the web or the laminate at a plurality of locations; U.S. Pat. No. 5,735,984 disclosing ultrasonic aperturing; U.S. Pat. Nos. 4,342,314 and 4,463,045 disclosing vacuum aperturing; U.S. Pat. Nos. 4,609,518; 4,629,643 and 4,695,422 disclosing hydroforming apertures; and U.S. Pat. No. 5,628,097 disclosing weakening a web along a plurality of locations and then applying a tensioning force to the web causing the web to rupture at the plurality of weakened location.

Referring to FIG. 4 there is schematically illustrated a process 100 for selectively aperturing a web. A web may comprise a polymeric film, nonwoven, or a composite or laminate comprising a polymer film layer and a nonwoven layer. A web 10 travels and passes through a nip 106 of the web weakening roller arrangement 108 formed by rollers 110 and 112.

Figure 5:
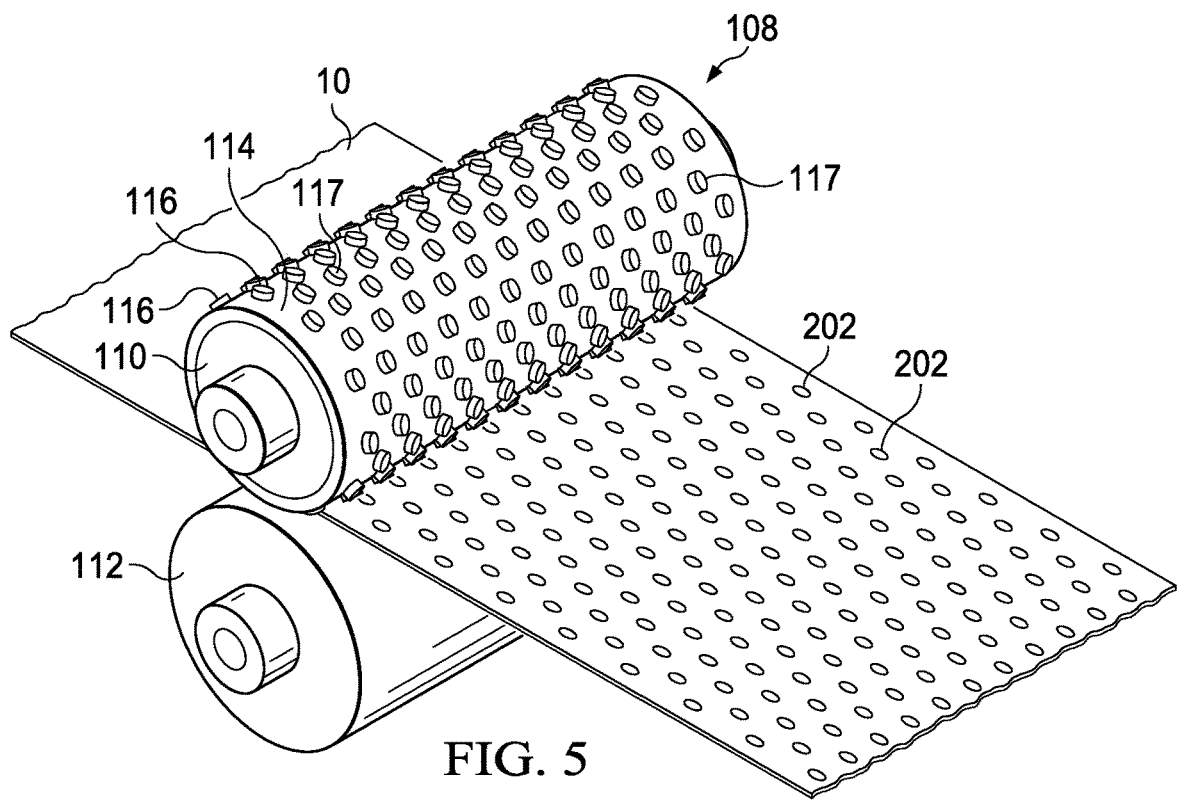
FIG. 5 is an enlarged perspective illustration of a web weakening arrangement of the process of FIG. 4.

Referring to FIGS. 4 and 5, the web weakening roller arrangement 108 preferably comprises a patterned calendar roller 110 and a smooth anvil roller 112. One or both of the patterned calendar roller 110 and the smooth anvil roller 112 may be heated and the pressure between the two rollers may be adjusted by well known means to provide the desired temperature, if any, and pressure to concurrently weaken and melt-stabilize the web 10 at a plurality of locations.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to precipitate a weakened, melt-stabilized location in the web 10 effect a predetermined pattern of weakened, melt-stabilized locations in the web 10. As shown in FIG. 5, patterned calendar roller 110 has a repeating pattern of protuberances 116 which extend about the entire circumference of surface 114. Alternatively, the protuberances 116 may extend around a portion, or portions of the circumference of surface 114.

The protuberances 116 are preferably truncated conical shapes which extend radially outwardly from surface 114 and which have elliptical distal end surfaces 117 although it is not intended to thereby limit the scope of the present invention to protuberances of only this configuration. Other suitable shapes for distal ends 117 include, but are not limited to circular, square, rectangular, etc. The roller 110 is finished so that all of the end surfaces 117 lie in an imaginary right circular cylinder which is coaxial with respect to the axis of rotation of roller 110.

The protuberances 116 are disposed in a regular predetermined pattern of rows and columns in the embodiment shown in FIG. 5, although it is not intended to thereby limit the scope of the present invention to the pattern of protuberances of only this configuration. The protuberances may be disposed in any predetermined pattern about patterned calendar roller 110.

Anvil roller 112 is preferably a smooth surfaced, right circular cylinder of steel.

Figure 6:
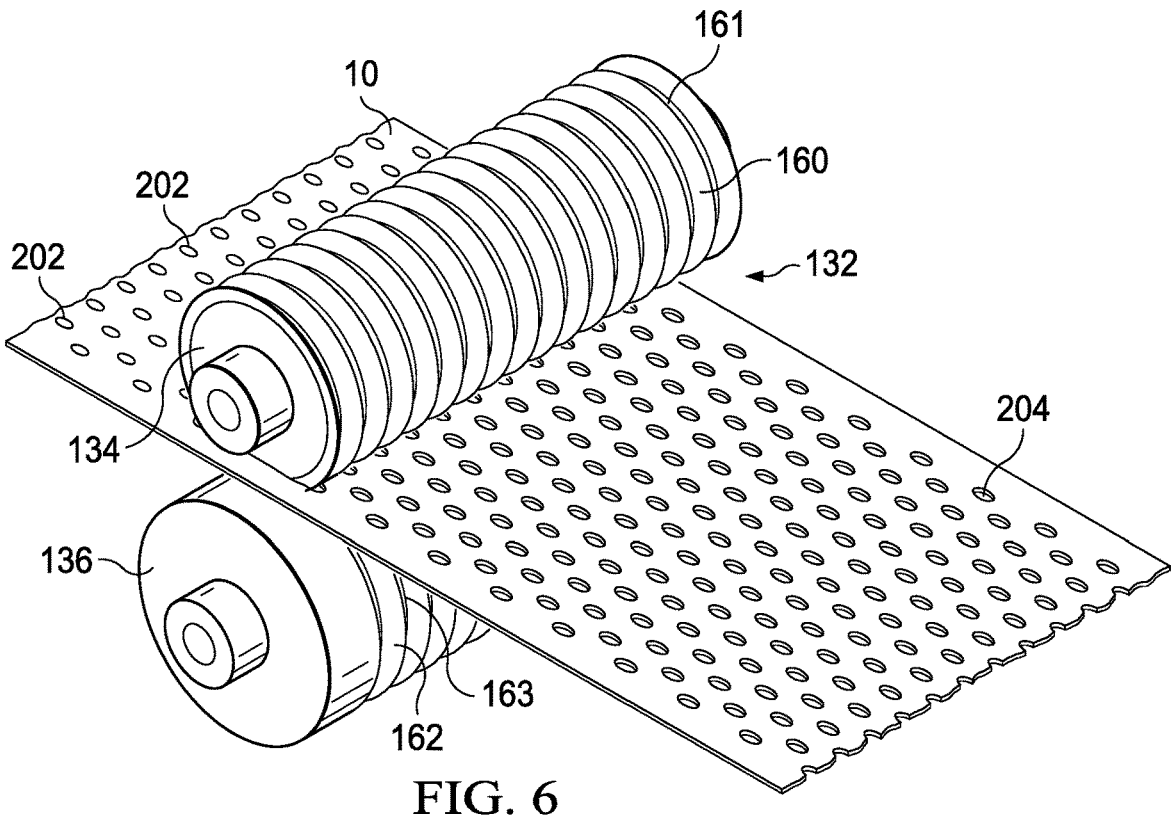
FIG. 6 is an enlarged perspective illustration of an incremental stretching system in the process of FIG. 4.

Referring now to FIG. 6, there is shown a fragmentary enlarged view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. As the web 10 having weakened, melt-stabilized locations 202 passes through the incremental stretching system 132 the web 10 is subjected to tensioning in the CD or cross-machine direction causing the web 10 to be extended in the CD direction. Alternatively, or additionally the web 10 may be tensioned in the MD or machine direction. The tensioning force placed on the web 10 is adjusted such that it causes the weakened, melt-stabilized locations 202 to rupture creating a plurality of apertures 204 coincident with the weakened melt-stabilized locations 202 in the web 10. However, the bonds of the web 10 are preferably strong enough such that they do not rupture during tensioning, thereby maintaining the web 10 in a coherent condition even as the weakened, melt-stabilized locations rupture. However, it may be desirable to have some of the bonds rupture during tensioning.

Other exemplary structures of incremental stretching mechanisms suitable for incrementally stretching or tensioning the web 10 are described in No. WO 95/03765, published Feb. 9, 1995 the disclosure of which is incorporated herein by reference.

The web 10 is preferably taken up on wind-up roller 180 and stored. Alternatively, the web 10 may be fed directly to a production line where it is used to form a topsheet on a disposable absorbent article.

Referring to FIG. 7 there is schematically illustrated at 300 another process for selectively aperturing a web. A web 10 travels and is forwarded through the weakening arrangement 308, and passed directly through the weakening arrangement 308.

Figure 8:
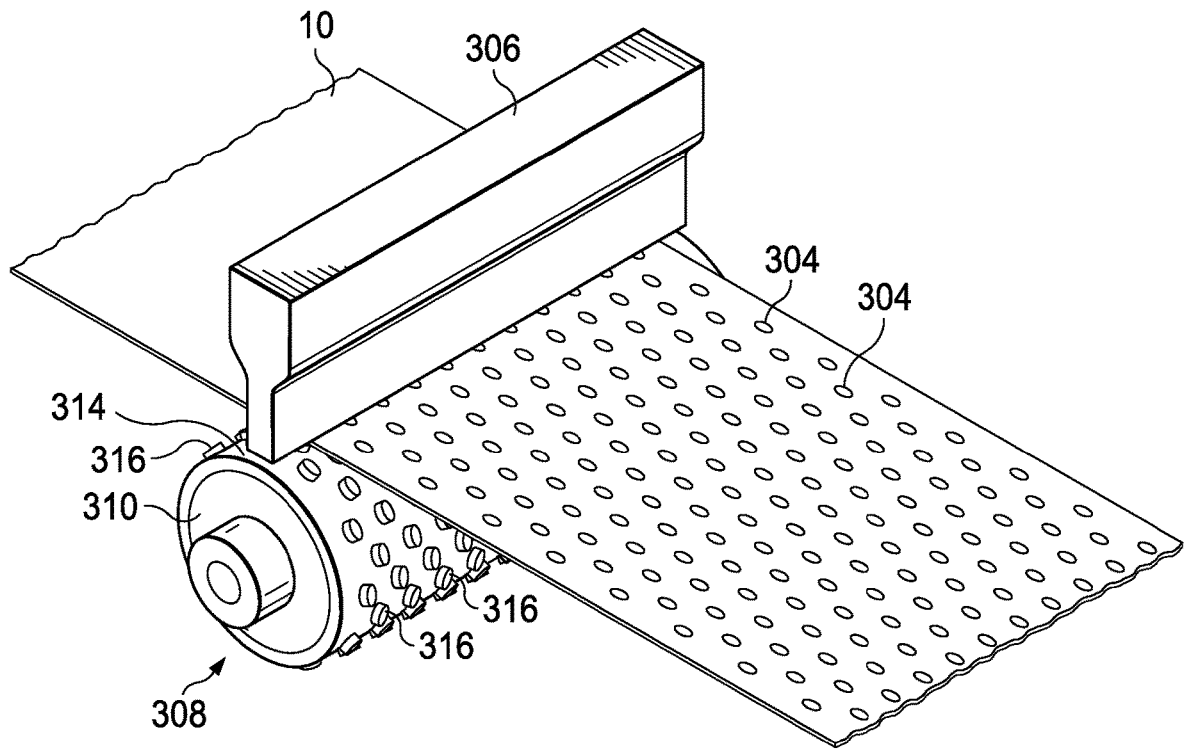
FIG. 8 is an enlarged perspective illustration of another web weakening arrangement of the process of FIG. 7.

Referring to FIGS. 7 and 8, the weakening arrangement 308 preferably comprises an ultrasonic transducer 306 and a cylinder 310. As the web 10 is forwarded between the ultrasonic transducer 306 and the anvil cylinder 310, the web 10 is subjected to ultrasonic vibrational energy whereupon predetermined pattern locations of the web 10 are weakened and melt-stabilized. Anvil cylinder 310 has a multiplicity of discrete pattern protuberances which are generally designated 316 disposed on its outwardly facing surface 314 in a predetermined pattern which extends about the entire circumference of the anvil cylinder. The protuberances 316 are disposed in a predetermined pattern with each protuberance 316 being configured and disposed to precipitate a weakened, melt-stabilized location 304 in the web 10 to effect a predetermined pattern of weakened, melt-stabilized locations in the web 10. As shown in FIG. 8, anvil 310 has a repeating pattern of protuberances 316 which extend about the entire circumference of surface 314. Alternatively, the protuberances 316 may extend around a portion, or portions of the circumference of surface 314.

The protuberances 316 are preferably truncated conical shapes which extend radially outward from the surface 314 and which have elliptical distal end surfaces. Other suitable shapes for the distal end include, but are not limited to, circular, square, rectangular, etc. The anvil 310 is finished so that all of the end surfaces lie in an imaginary right circular cylinder which is coaxial with respect to the axis of rotation of anvil cylinder 310.

After having passed through the weakening arrangement 308, and prior to passing through the nip 330 of the incremental stretching system 332, the web 10 includes a plurality of weakened, melt-stabilized locations 304 which generally correspond to the pattern of protuberances 316 extending from the surface 314 of anvil cylinder 310.

From the weakening arrangement 308, the web 10 passes through nip 330 formed by the incremental stretching system 332 employing opposed pressure applicators having three-dimensional surfaces which at least to a degree are complementary to one another. The incremental stretching system 332 preferably comprises incremental stretching rollers 334 and 336. The incremental stretching roller 334 includes a plurality of teeth and corresponding grooves which extend about the entire circumference of the roller 334. Incremental stretching roller 336 includes a plurality of teeth and a plurality of corresponding grooves. Teeth on roller 334 intermesh or engage with the grooves on roller 136, while the teeth on roller 336 intermesh with or engage with the grooves on the roller 334. As the web 10 having weakened, melt-stabilized locations 304 passes through the incremental stretching system 332, the web 10 is subjected to tensioning causing the web 10 to be extended. The tensioning force placed on the web 10 is adjusted such that it causes the weakened, melt-stabilized locations 304 to rupture creating a plurality of apertures in the web 10 which are coincident with the weakened melt-stabilized locations.

One type of discrete features preferred for the second discrete features in the present invention especially when at least one of the first and second layers is nonwoven are tufts. In many applications, it is desirable that fibrous webs have a bulky texture and/or softness. Composites in which nonwoven fibers protrude or are partially exposed through a polymer film or nonwoven can be useful as a topsheet in absorbent articles as they provide an absorbent structure in which the nonwoven acts as the conveyor of fluid. As a non-limiting example, the composite comprises a polymer film and a nonwoven structured such that the fluid collecting side of the composite is the polymer film, and nonwoven fibers protrude or are partially exposed through the polymer film to the fluid collecting side of the composite.

Various methods and apparatuses for forming tufts disclosed in patent literature. Patents disclosing such methods include: U.S. Pat. Nos. 3,485,706, 4,465,726 and 4,379,799 disclosing forming tufts using waterjet; U.S. Pat. No. 4,741,941 disclosing forming tufts using air drawing, U.S. Pat. No. 5,080,951 disclosing a needle punching method; and WO 1994/058117, WO 2004/59061, and WO 2010/117636 disclosing a method for making tufts on a web using an apparatus comprising a roller comprising a plurality of ridges and grooves.

In one embodiment, the first discrete features are formed by feeding a first layer in a machine direction into a first nip that is formed between two generally cylindrical rollers, the two rollers having surfaces wherein at least one of the two rollers has first discrete feature forming elements on its surface, and when the first layer is fed into the nip, the first layer is deformed.

In another embodiment, the second discrete features are formed by feeding a composite of a first layer and a second layer in a machine direction into a second nip that is formed between two generally cylindrical rollers, the two rollers having surfaces wherein at least one of the two rollers has second discrete feature forming elements on its surface, and when the composite is fed into the nip, the composite is deformed. The two rollers forming the first discrete features and the two rollers forming the second discrete features can be separate pairs of rollers.

Figure 10:
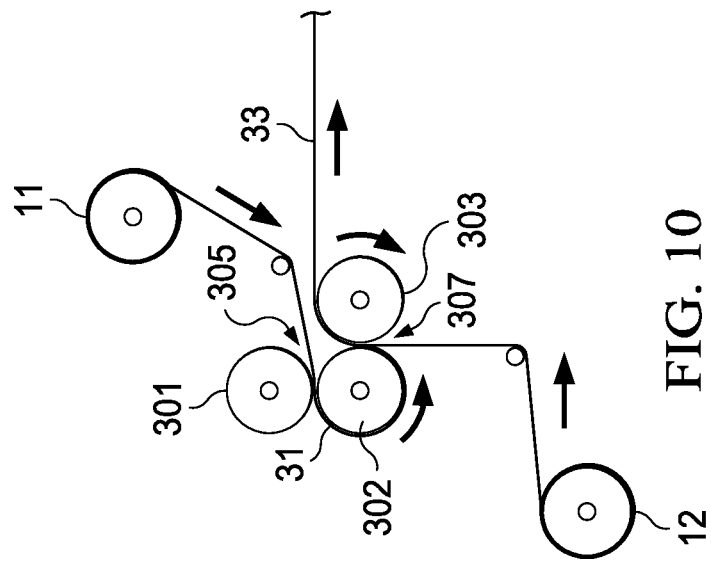
FIG. 10 is a schematic representation of another means of forming a first and a second discrete feature as separate forming steps of a process of the present invention.

In another embodiment, the two rollers forming the first discrete features and the two rollers forming the second discrete features can share one roller between the two pairs of rollers. As shown in FIG. 10, the first discrete features are formed by feeding a first layer 11 in a machine direction into a first nip 305 that is formed between a first generally cylindrical roller 301 and a second generally cylindrical roller 302, and a deformed first layer 31 is prepared. Continuously, the second discrete features are formed by introducing the deformed first layer 31 and a second layer 12 in a machine direction into a second nip 307 that is formed between the second generally cylindrical roller 302 and a third generally cylindrical roller 303, forming a deformed composite 33. The first roller 301 is a ring roller, the second roller 302 has the first discrete feature forming elements on its surface in some zones and continuous rings for mating with the second discrete feature forming elements in separate zones, and the third roller 303 has the second discrete forming elements on its surface. This results in first and second discrete features formed in opposite directions.

The rollers used in the apparatuses and methods described herein are typically generally cylindrical. The term "generally cylindrical", as used herein, encompasses rolls that are not only perfectly cylindrical, but also cylindrical rollers that may have elements on their surface. The term "generally cylindrical" also includes rollers that may have a step-down in diameter, such as on the surface of the roller near the ends of the roller. This can enable forming deformed elements of different heights in respective zones of the same roller. The rollers are also typically rigid (that is, substantially non-deformable).

WO 2012/148935 discloses several mechanical deformation processes for forming discrete features such as an approach utilizing a single nip with two rollers comprising discrete male forming elements wherein at least one roller comprises two or more raised ridges, and another approach comprising a multi-hit (multi-nip) configuration that enables controlled placement and orientation of multiple sets of features. Each of these approaches may enable independent control of the features formed in a multi-layer structure, providing additional control over the function and aesthetics of the features. For example, this process could provide the ability to create multi-layer structures where some features have more layers through their thickness than other features.

In one embodiment, the first discrete feature forming elements or the second discrete feature forming elements can be heated.

In one embodiment when a plurality of the first and/or second discrete features are apertures, the first and/or the second discrete feature forming elements can comprise rounded teeth or triangular shaped teeth disclosed in WO 2005/13874. Alternatively, in the embodiment, the first and/or the second discrete feature forming elements can comprise being tapered from a base and a tip wherein the base of each tooth has a cross-sectional length dimension greater than a cross-sectional width dimension, wherein each tooth is oriented such that the cross-sectional length dimension of the tooth is disposed at an angle greater than zero relative to a predominant molecular orientation of a first and/or second layer as described in WO 2010/90974.

In another embodiment, the first layer may be ring rolled with intermeshing rolls prior to the first discrete feature forming step as described in WO 2010/90974. Ring-rolling of the first layer prior to forming the first discrete features, especially apertures, is expected to result in an increase in the size of the apertures and increase in the air permeability of the first layer.

In another embodiment, the deformed composite 33 or 43 may be ring rolled with intermeshing rolls after forming the second discrete features, especially after forming apertures, to spread the apertures apart after formation.

In another embodiment when a plurality of second discrete features are tufts, the second discrete feature forming elements can comprise a plurality of ridges and corresponding grooves which extend unbroken about the entire circumference of a roller which has the second discrete feature forming elements discloses in WO 2004/59061 and WO 2010/117636. The tufts may comprise a plurality of tufted fibers being integral extensions of the nonwoven. In another embodiment when the second layer is nonwoven and a plurality of second discrete features are tufts, at least part of the distal portion of each of the tufts is covered by a cap, each cap being an integral extension of the first layer extending over the distal portion of a discrete tuft.

Provision of a Colored Region on Colored Sheet Web

In the present invention, a first colored region on a colored sheet web can be provided by various methods and apparatus well known to those skilled in the art such as lithographic, screen printing, flexographic, gravure ink jet printing techniques or a method of producing color change using an activatable colorant, and virtually any graphic in any color or color combination can be rendered on the colored sheet web colored sheet web. Patents disclosing such methods include: U.S. Pat. No. 7,736,688 disclosing flexographic printing; WO 2011/25486 disclosing a method of manufacturing an absorbent article having two colored regions and a method of color measurement; and WO2011/133464 and WO2011/133462 disclosing a method of producing color change on a web using an activatable colorant.

Supplying and Integration of Colored Sheet Web

A colored sheet web having a first colored region is introduced by an apparatus, such as a roller, onto the second layer side of the deformed composite of a first layer and a second layer where first and second discrete features are formed, and the colored sheet web and the deformed composite are both moving in a machine direction. The colored sheet web can be introduced to the deformed composite as either a continuous layer or a discrete sheet cut before supplied onto the deformed composite into a predetermined size and shape. A discrete sheet of the colored sheet web having a first colored region can be prepared by printing a plurality of first colored regions on a continuous liquid pervious colored sheet web and cutting the continuous liquid pervious colored sheet web into discrete sheets in a predetermined shape and size using a cutting means well known to those skilled in the art. The exact dimensions of the size and shape of the discrete sheets may be determined depending on type of an absorbent article. In one example, the colored sheet comprising a colored sheet web is in size and shape which is shorter in length than the final length of an absorbent article such that fluid cannot be transported or wicked to the end of the article. In another embodiment, the colored sheet comprising a colored sheet web extends to the periphery of the topsheet so that the colored sheet web layer underlies the topsheet on the entire inner surface of the topsheet. In the method according to the present invention, a colored sheet web and a composite of the first layer and the second layer can be integrated by various methods and apparatus known to those skilled in the art. For examples, the integration can be carried out by a process selected from the group consisting of cold pressure bonding, heated pressure bonding, ultrasonic bonding, gluing and combinations thereof. Patents disclosing such methods include: U.S. Pat. Nos. 4,854,984 and 4,919,738 for cold pressure bonding.

In one embodiment, a colored sheet web having a first colored region, and a composite of a first layer and a second layer can be integrated by heated pressure bonding method comprising forwarding a composite of the colored sheet web and the composite through a generally cylindrical pattern defining roller and a mating anvil roller. The generally cylindrical pattern defining roller and mating anvil roller may be rotated at matched speeds or at differing speeds to one another.

Supplying and Integrating Backsheet Web

A backsheet web can be supplied by an apparatus such as an adhesive bonding roller or thermal sealing roller onto a colored sheet web side of the integrated composite 34, 44 which are moving in a machine direction to form an absorbent article assembly 36, 46. When an absorbent core is optionally provided onto the integrated composite, the backsheet web can be introduced onto an absorbent core side of the core layered composite 45.

The backsheet web is integrated to the integrated composite so that in an absorbent article a backsheet is preferentially peripherally joined with a topsheet using known techniques, either entirely so that the entire perimeter of the sanitary article is circumscribed by such joinder or are partially peripherally joined at the perimeter.

Supplying and Integrating Backsheet web

The absorbent article assembly is severed or cut using by a cutting unit conventional in the technical area of absorbent article fabrication into individual absorbent articles to have a predetermined size and shape.

Optional Steps

Registration

Absorbent articles comprise multiple functional and/or aesthetic components including compositional elements such as a topsheet, a backsheet and optionally secondary topsheet and an absorbent core, and design elements such as colored regions, discrete features formed on a topsheet, and optionally channels and a logo. During the manufacturing of absorbent articles, the position of components of article in each step of the manufacturing process may affect the overall quality of the articles and the acceptance of the articles by consumers as consumers often desire consistency in the configuration of purchased goods for both functional and aesthetic reasons. For example, locations of the first discrete features, the second discrete feature, the first colored region and/or the second colored region need to be controlled as designed to secure best functional and aesthetic goods. To ensure consistency throughout the manufacturing process, components must be positioned uniformly.

Various methods and systems for inspecting the locations of selected components of an absorbent article during a manufacturing process have been known. Patents disclosing such methods and systems include: U.S. Pat. No. 5,359,525; EP 2090 951 A1; and WO 2012/161709 disclosing system and method of the automated regulation of production lines.

In a method according to the present invention, a phasing can be conducted in between two consecutive steps to determine and control position of at least one component, and may be carried out at least once.

Formation of a Plurality of Discrete Extended Elements

A method according to the present invention optionally comprises a step of forming a plurality of discrete extended elements on a first layer, or a composite of a first layer and a second layer when at least the first layer is a polymer film. Hereinafter in this section of Formation of a Plurality of Discrete Extended Elements, a first layer, and a composite of a first layer and a second layer are collectively denoted as a precursor web. It can be beneficial for the precursor web to have a textured surface by having a plurality of discrete extended elements which can provide the surface of the polymer film with a desirable feel, visual impression, and/or audible impression.

A plurality of discrete extended elements can be made in a vacuum forming process, a hydroforming process, a high static pressure forming process, a solid state deformation process in mated forming structures, or methods using a forming structure and a compliant substrate. With a typical vacuum forming process, a precursor web is heated and placed over a forming structure. Then a vacuum forces the precursor web to conform to the texture of the forming structure. The resulting web has texture that can provide a soft and silky tactile impression, depending upon the texture of the forming structure and degree of conformation. With a typical hydroforming process, a precursor web is placed over a forming structure and high pressure and high temperature water jets force the precursor web to conform to the texture of the forming structure. A high static pressure forming process employs a high pressure gas to deform the precursor web to the texture of a forming structure as disclosed in WO 10/105002, WO 10/105017 and WO 11/112213, while solid state deformation conveys the web between mating forming structures as disclosed in WO 12/148936, or uses a compliant substrate to impress the discrete extended elements into the precursor web as disclosed in WO 10/105009 and WO 10/105019.

A plurality of discrete extended elements in the present invention, especially when the first layer is a polymer film, comprise open proximal ends, open or closed distal ends, and sidewalls, wherein the discrete extended elements comprise thinned portions at the distal ends of the discrete extended elements and/or along the sidewalls of the discrete extended elements, and wherein (a) the discrete extended elements have a diameter of less than about 500 microns, (b) the discrete extended elements have an aspect ratio of at least about 0.2, and/or (c) the polymer film comprises at least about 95 discrete extended elements per square centimeter.

In an embodiment, a plurality of discrete extended elements can be formed by a process comprising the steps of: i) providing a forming structure comprising a plurality of discrete protruded elements and lands completely surrounding the discrete protruded elements; ii) providing a compliant substrate; iii) providing a precursor web between the compliant substrate and the forming structure, and iv) providing pressure between the compliant substrate and the forming structure sufficient to conform the precursor web to the discrete protruded elements of the forming structure to form the embossed web.

In another embodiment, a plurality of discrete extended elements can be formed by a process comprising the steps of: i) feeding a precursor web between a static gas pressure plenum and a forming structure comprising a plurality of discrete protruded elements, the discrete protruded elements having a height of at least substantially equal to a thickness of the precursor web; and ii) applying pressure from the static gas pressure plenum against the precursor web opposite the forming structure creating a pressure differential across the precursor web sufficient to conform the precursor web to the discrete protruded elements of the forming structure.

In another embodiment, a plurality of discrete extended elements can be formed by a process comprising the steps of: i) feeding a precursor web between a static gas pressure plenum and a forming structure comprising a plurality of discrete apertures, discrete depressions, or combinations thereof, the apertures or depressions having a depth of at least substantially equal to a thickness of the precursor web; and ii) applying pressure from the static gas pressure plenum against the precursor web opposite the forming structure creating a pressure differential across the precursor web sufficient to force the precursor web into the apertures or depressions of the forming structure, thereby forming the precursor web comprising a plurality of discrete extended elements.

In another embodiment, a plurality of discrete extended elements can be formed by a process comprising the steps of: i) providing a precursor web, ii) providing a pair of mated forming structures, including a first forming structure and a second forming structure, wherein at least the first forming structure comprises voids, and wherein at least the second forming structure comprises protrusions; and iii) moving the web through a deformation zone between the mated forming structures, wherein the voids of the first forming structure engage with the protrusions of the second forming structure at an engagement position.

Provision of a Second Colored Region

A method according to the present invention optionally comprises a step of providing a second colored region on the first layer or the second layer either prior to or after formation of the first discrete features. The second colored region can be provided either side of the first layer or the second layer. Regarding coloration methods, descriptions in the section of Provision of a Colored Region on Colored Sheet above are applicable for provision of the second colored region.

Introduction of Absorbent Core

A method according to the present invention optionally further comprises a step of supplying and integrating an absorbent core to a colored sheet web side of the integrated composite 34, 44 moving in a machine direction to form a core layered composite 35, 45. The absorbent core can be supplied as a preformed core. In one embodiment, the absorbent core is cut in a predetermined size and shape before being provided onto the colored sheet web side of the integrated composite.

An absorbent core can be integrated to the integrated composite by various methods and apparatus known in the art such as cold pressure bonding, heated pressure bonding, ultrasonic bonding, gluing and combinations thereof. In one embodiment, an absorbent core can be integrated to the core layered composite by gluing.

Application of Lotion Composition

Treatments of an absorbent article with lotion have been proposed to provide skin health benefits and to allow fluid to be absorbed into the article. To provide an absorbent article treated with a lotion, a method of the present invention may further comprise a step of applying a lotion composition to at least a portion of a topsheet, the inner surface of the backsheet, and/or any substrate (or surface thereof) disposed between the topsheet and the backsheet such as a secondary topsheet and an absorbent core. The lotion composition can be a liquid, a solid or a semi-solid at room temperature, and comprise at least one skin benefit agent. The lotion composition can be applied in any known manner, in any known pattern, and to any known portion of the absorbent article, as is well known in the art of lotioned absorbent articles. For example, the lotion composition can be applied in a pattern of generally parallel stripes or bands. The lotion composition can be a lotion coating on any part of the article, and on either side of any layer, such as upper surfaces, or lower surfaces. In one embodiment, a lotion composition can be disposed on the inner surface of the topsheet by disposing the lotion composition on at least one of a lower side of a first layer, an upper side and a lower side of a second layer. The lotion can be applied prior to the first discrete forming step, after the first discrete forming step and/or after the second discrete forming step.

Application of Odor Control Composition

A method of the present invention may further comprise a step of applying an odor control composition. Use of a fragrance composition and/or an odor control composition in absorbent articles has been proposed for controlling and reducing malodors in the articles. In general, suitable components for odor control compositions include reactive components. Reactive components include components that can react with malodors, such as ammonia-based malodors or sulphur-based malodors (i.e. "malodor reactive components"), and components that mask malodors and/or react with receptors of the nose to block the perception of malodor by the nose of a consumer (i.e. "malodor masking components"). Suitable reactive components are described, for example, in US 2008/0071238A1 and WO 07/113778, and suitable masking components are described, for example, in WO 08/114226.

An odor control composition may be applied on or within a layer of an absorbent article in any known manner, in any known pattern, and to any known portion of the absorbent article, as is well known in the art of absorbent articles. This means that, since the absorbent article is constituted by a series of layers, the odor control composition is applied onto one of the surfaces of these layers. An odor control composition can be applied onto the surface of application with any possible application pattern. In some cases it is possible that the odor control composition is applied on more than one layer within the article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for fabricating an absorbent article, the absorbent article comprising a liquid permeable topsheet comprising a first layer, a second layer; a colored sheet comprising a colored sheet web having a first colored region; and a liquid impermeable backsheet comprising a backsheet web, the absorbent article having a body-facing surface comprising the first layer and a garment-facing surface positioned opposite to the body-facing surface, the method comprising the steps of:
    a) obtaining a composite of the first layer and the second layer, wherein the composite comprises a first plurality of discrete features;
    b) forming a second plurality of discrete features in the composite of the first layer and the second layer, wherein the first plurality of discrete features differ from the plurality of second discrete features;
    c) obtaining the colored sheet web having the first colored region onto the second layer side of the composite, and integrating the composite and the colored sheet web to form an integrated composite;
    d) supplying the backsheet web onto the colored sheet web side of the integrated composite, and integrating the integrated composite and the backsheet web to form an absorbent article assembly; and
    e) severing the absorbent article assembly into individual absorbent articles, wherein the absorbent article has a background region, wherein the background region and the first colored region are viewable from the body facing surface, and wherein the first colored region differs in color from the background region.

2. The method according to claim 1, wherein the first layer in step a) comprises a plurality of discrete extended elements, wherein the discrete extended elements comprise open proximal ends, open or closed distal ends, and sidewalls, wherein the discrete extended elements comprise thinned portions at the distal ends of the discrete extended elements and/or along the sidewalls of the discrete extended elements, and wherein
    a) the discrete extended elements have a diameter of less than about 500 microns;
    b) the discrete extended elements have an aspect ratio of at least about 0.2; or
    c) the first layer comprises at least about 95 discrete extended elements per square centimeter.

3. The method according to claim 2, wherein the first layer in step a) further comprises apertures wherein the apertures have a diameter bigger than that of the plurality of discrete extended elements.

4. The method according to claim 3, further comprising a step of providing the first layer with a second colored region by a second coloration technique carried out prior to step c), wherein the first colored region and the second colored region differ in color from the background region.

5. The method according to claim 3, wherein the first discrete features are features selected from the group consisting of apertures, protrusions, depressions, tufts and combinations thereof.

6. The method according to claim 3, further comprising a step of determining and controlling positions of at least one component of the absorbent article at least once during steps a) through d).

7. The method according to claim 3, wherein the first layer and second layer of the composite are integrated by an integration process selected from the group consisting of cold pressure bonding, heated pressure bonding, ultrasonic bonding, gluing and combinations thereof.

8. The method according to claim 1, further comprising a step of providing at least one of the first layer and the second layer with a second colored region by a second coloration technique, wherein the first colored region and the second colored region differ in color from the background region.

9. The method according to claim 1, further comprising a step of determining and controlling positions of at least one component of the absorbent article at least one time between steps a) through d).

10. The method according to claim 1, wherein the first layer and second layer of the composition are integrated by an integration process selected from the group consisting of cold pressure bonding, heated pressure bonding, ultrasonic bonding, gluing and combinations thereof.

11. The method according to claim 1, wherein the first layer is selected from a group consisting of polymer film, a nonwoven and a combination thereof, and the second layer is selected from a group consisting of a polymer film, a nonwoven and a combination thereof.

12. The method according to claim 1, wherein the composite of the first layer and the second layer comprises a film layer and a nonwoven layer.

13. The method according to claim 12, wherein the nonwoven layer is a spunbonded nonwoven.

14. The method according to claim 12, wherein the nonwoven layer is a carded nonwoven.

15. The method according to claim 1, wherein the composite of the first layer and the second layer comprises a first nonwoven layer and a second nonwoven layer.

16. The method of claim 2, wherein the discrete extended elements are formed via hydroforming or vacuum forming.

17. The method of claim 1, wherein the colored sheet comprises a nonwoven material.

18. A method for fabricating an absorbent article, the absorbent article comprising a liquid permeable topsheet comprising a first layer, a second layer; a colored sheet comprising a colored sheet web having a first colored region; and a liquid impermeable backsheet comprising a backsheet web, the absorbent article having a body-facing surface comprising a polymer film and a garment-facing surface positioned opposite to the body-facing surface, the method comprising the steps of:
   a) obtaining a composite or laminate of the first layer and the second layer, wherein the composite comprises a plurality of first discrete features and a plurality of second discrete features, wherein said plurality of second discrete features differ from said plurality of first discrete features;
   b) supplying the colored sheet web having the first colored region onto the second layer side of the composite or laminate, and integrating the composite or laminate and the colored sheet web to form an integrated structure;
   c) supplying the backsheet web onto the colored sheet web side of the integrated structure, and integrating the integrated structure and the backsheet web to form an absorbent article assembly; and
   d) severing the absorbent article assembly into individual absorbent articles, wherein each absorbent article has a background region, wherein the background region and the first colored region are viewable from the body facing surface, and wherein the first colored region differs in color from the background region.

19. The method according to claim 18, wherein the first discrete features are features selected from the group consisting of apertures, protrusions, depressions, tufts and combinations thereof, and the second discrete feature are features selected from the group consisting of apertures, protrusions, depressions, tufts and combinations thereof.

20. The method according to claim 18, further comprising a step of determining and controlling positions of at least one component of the absorbent article at least once between steps (a) through (d).

* * * * *